United States Patent
Phillips et al.

(10) Patent No.: US 6,497,666 B1
(45) Date of Patent: Dec. 24, 2002

(54) MEDICAL ULTRASONIC CONTRAST AGENT IMAGING METHOD AND APPARATUS

(75) Inventors: Patrick J. Phillips, Sunnyvale, CA (US); Ismayil M. Guracar, Redwood City, CA (US)

(73) Assignee: Acuson Corporation, Mountain View, CA (US)

( * ) Notice: Subject to any disclaimer, the term of this patent is extended or adjusted under 35 U.S.C. 154(b) by 32 days.

(21) Appl. No.: 09/696,511

(22) Filed: Oct. 25, 2000

(51) Int. Cl.[7] .................................. A61B 8/14
(52) U.S. Cl. ........................................ 600/458
(58) Field of Search ........................ 600/437, 439, 600/440–447, 454, 458; 73/625, 626, 602

(56) References Cited

U.S. PATENT DOCUMENTS

| | | |
|---|---|---|
| 5,255,683 A | 10/1993 | Monaghan |
| 5,456,257 A | 10/1995 | Johnson et al. |
| 5,632,277 A | 5/1997 | Chapman et al. |
| 5,706,819 A | 1/1998 | Hwang et al. |
| 5,833,613 A | 11/1998 | Averkiou et al. |
| 5,908,389 A * | 6/1999 | Rooundhill et al. ........ 600/443 |
| 5,951,478 A | 9/1999 | Hwang et al. |
| 5,961,460 A | 10/1999 | Guracar et al. |
| 6,095,980 A | 8/2000 | Burns et al. |

OTHER PUBLICATIONS

"Harmonic Power Mode Doppler Using Microbubble Contrast Agents: An Improved Method for Small Vessel Flow Imaging", by Peter Burns, J. Powers, D. Simpson, A Brezina, A. Kolin, C. Chin, V. Uhlendorf, and T. Fritzsch, 1994 Ultrasonics Symposium, Nov. 1–4, 1994 Hotel Martinez, Cannes, France; An International Conference of the IEEE Ultrasonics, Ferroelectrics, and Frequency Control Society.

* cited by examiner

Primary Examiner—Marvin M. Lateef
Assistant Examiner—Ali M. Imam (57) ABSTRACT

A medical ultrasonic imaging system transmits a set of two or more substantially identical transmit pulses into a tissue containing a contrast agent. The associated received pulses are filtered with a broadband filter that passes both the fundamental and at least one harmonic component of the echoes. The filtered received pulses are then applied to a clutter filter that suppresses harmonic and fundamental responses from slowly moving and stationary tissue, while clearly showing contrast agent response due to the loss of correlation effect. The disclosed system includes other signal paths for generating conventional B-mode images as well as combined images that include both components from the contrast-specific image as well as components from the B-mode image. An improved user interface allows the user to switch among these three images. Preferably the transmitter generates transmitted pulses having two or more spatially distinct focus zones, thereby improving the uniformity of contrast agent imaging over the imaged region.

42 Claims, 6 Drawing Sheets

MEDICAL ULTRASONIC CONTRAST AGENT IMAGING METHOD AND APPARATUS

BACKGROUND

This invention relates to medical ultrasonic imaging, and in particular to systems for improved imaging of contrast agent included in imaged tissue.

The nonlinear response of contrast agents such as microbubbles improves the detectability of microbubbles in tissue. Contrast agents effectively generate unique ultrasound signals such as second harmonic, third harmonic, subharmonic, or other harmonics that are not transmitted in significant quantities by a transducer. Good second harmonic contrast agents, in particular, have been shown to generate strong signals with minimal destruction of a population of contrast microbubbles.

Another unique property of contrast agents is that they are disrupted by impinging sound waves. Ultrasound pulses in particular can move, crack, rearrange, split, and destroy microbubbles and their gas-encapsulating shells. When this type of disruption occurs, at least two received pulses will be decorrelated when at least two identical pulses are transmitted during at least two separate transmit events. A loss-of-correlation (LOC) between received signals may be used to detect contrast agents, since areas that contain little or no contrast agent will return similar signals among the multiple received pulses and produce strong signal correlations.

There is a need for an improved LOC imaging technique that offers excellent specificity for contrast agents, high bandwidth resolution, and high frame rates. Further, there is a need to increase the spatial uniformity of detected contrast agents within an image frame when LOC techniques are implemented. Still further, there is a need to offer a contrast-only image that may or may not be displayed with an image substantially free of detected contrast agent.

Among the prior-art techniques for detecting contrast agents at least five disadvantages exist, as follows.

1.) Poor Axial Resolution Due to Narrowband Receive Filtering

A technique often labeled as "harmonic imaging" specifically filters each received pulse/signal with the goal of suppressing fundamental energy and retaining second harmonic energy. This technique limits the bandwidth of returned signals and therefore limits axial resolution. "Power Harmonics" by ATL or harmonic "Power Contrast Imaging" (PCI) by Acuson are two examples of this technique. Since the ratio of returned contrast agent energy to tissue energy for second harmonic signals is typically larger than the ratio of returned contrast agent energy to tissue energy for fundamental signals, second harmonic signals have been preferred for imaging contrast agents. By adequately suppressing fundamental energy by filtering each received pulse separately within a set of multiple received pulses, less tissue flash is introduced into the images if a clutter filter is applied across the two or more received pulses at each range. The purpose of the clutter filter is to remove signals from stationary or slowly moving targets. Since returned fundamental signals are the largest amplitude signals returned from stationary or slowly moving tissue as compared to harmonic signals, separately pre-filtering each returned pulse with a narrowband filter that suppresses fundamental energy reduces the amount of stopband rejection and/or stopband width required of the clutter filter. Fewer taps may be used with these types of clutter filters, and therefore fewer pulses need to be transmitted, thereby improving frame rates and minimizing unnecessary agent destruction.

Other examples of prior art that selectively filters second harmonic signals include "Harmonic Power Mode Doppler . . . " by Burns et. al [1] and "Ultrasonic Diagnostic Imaging with Contrast Agents" by Averkiou [2]. The former reference specifically describes a narrow-band digital filter in the Instrumentation subsection of the Methods section. The latter specifically describes the desire for narrowband filtering in Col. 5, lines 23 through 35, with reference to FIG. 6, and Col. 6, lines 13–19. Full citations for these and the other references cited in this section are provided in Table 1.

In other prior-art systems that selectively image the fundamental signal and suppress the second harmonic signal, e.g., the fundamental PCI imaging mode offered by Acuson, axial resolution is similar or inferior to those techniques that specifically suppress fundamental frequency components and retain second harmonic frequency components.

2.) Inability to Separate an Anatomical Reference Image from a Contrast-Only Image The two-pulse, alternate polarity techniques (U.S. Pat. Nos. 5,706,819 [3], 5,951,478 [4], and 5,632,277 [5]) and multiple-pulse alternate polarity techniques ("Pulse Inversion Doppler" U.S. Pat. No. 6,095,980 [6]) and some Contrast Pulse Sequences (Reference [7]) are unable to show an accurate second harmonic contrast-only image, since tissue second harmonic signals cannot be accurately separated from contrast agent second harmonic signals. Techniques that alternate the transmit envelope polarity between different transmit events modulate the fundamental frequency signal components into the stopband of a clutter filter, which is applied across multiple received pulses at a single point in space, while second harmonic frequency signal components remain unmodulated and minimally suppressed by the passband of the clutter filter. Since the second harmonic signals generated from nonlinear propagation through tissue are not adequately suppressed, a stationary or slowly moving tissue image is inherently integrated with detected contrast agent signals. This is most significant for high mechanical index (MI) imaging, where tissue harmonic signals are strong. This is a significant clinical limitation, since contrast-only images can look much different than images that integrate contrast agent information with anatomical information.

Techniques that can generate contrast-only images can offer additional diagnostic information not available from techniques that alternate the transmit envelope polarity between different transmit events. For example, a 1 cm diameter lesion as seen in a B-mode image may appear as a 0.5 cm diameter lesion in a contrast-only image due to strongly anechoic areas near the perimeter of the lesion absorbing contrast agents. Without the ability to separate these two types of images after the acquisition and detection of a single frame, diagnostic confidence is reduced. Contrast-only image information can facilitate more accurate diagnosis and provide functional information.

3.) Inability to Pre-Scan a Region Before Imaging with a Contrast-Specific Imaging Technique Current techniques used for contrast agent imaging such as the two-pulse techniques mentioned above lack the ability to pre-scan a region at low power before generating an image showing detected contrast agent with high specificity. For some contrast agents, such as Levovist, high MI scanning is preferred for achieving high agent specificity. However, high MI scanning disrupts the contrast agent, and can quickly deplete a region of contrast agent. Imaging techniques that inherently integrate anatomical tissue signals with contrast-specific signals do not facilitate efficient acquisition and user-selectable display of high-specificity contrast agent images. Once the transducer is placed on the subject, contrast agent is immediately disrupted and depleted. Pre-scanning with an alternating polarity pulsing technique at low transmit power to locate an area of interest and then manually turning up the transmit amplitude/power can be used, but contrast agent is destroyed before the optimal maximum transmit power is reached. Thus, unnecessary agent destruction occurs before the high specificity contrast agent image is generated. Further, optimal specificity may not be possible due to the lesser contrast agent concentration. A manually-activated, instantaneous, substantial increase in transmit power would be useful, but the inability to separate the background image from the contrast-only image still makes this type of technique suboptimal. The current procedure used with the alternating-polarity pulsing techniques is to begin a sweep through an organ, such as the liver, and hope to capture a slice, or slices, of interest through the organ. There often exists the possibility that a small lesion may have been missed, reducing diagnostic confidence, and demanding the need for further scanning and possibly further contrast agent injections.

4.) Insufficient Agent Specificity and Poor Sensitivity to Slow Flow or Small Variations Between Received Pulses from Separate Transmit Events Incoherent LOC techniques have been disclosed that detect the presence of contrast agents within each received pulse and then subtract the two resulting detected signals. These phase-insensitive techniques can be less susceptible to color flash, or tissue flash, due to movement between transmitted pulses, but these techniques lack the sensitivity to small variations between received pulses. This reduces specificity and sensitivity. Examples of such incoherent techniques are disclosed in references [8] and [9].

5.) Poor image uniformity throughout an image displaying detected contrast agent Conventional contrast agent imaging utilizes a focused transmit beam that generates a dominant focus with a specific focal region of high peak pressure. A single focus during a single transmit event generates excellent lateral resolution at or near the focal region, but fails to distribute peak pressures uniformly over a large depth-of-field, or section of ranges. Small transmit apertures can increase the depth-of-field uniformity, but at the expense of lesser transmit pressures in the field containing the contrast agents and degraded lateral resolution. A technique disclosed in reference [2] describes a method of stitching together received signals from multiple transmit events after a transmit focus has been moved between each transmit event. The resultant signal for a specific zone is most heavily weighted by the transmit event that sets the transmit focus within the specific zone of interest, as discussed at col. 9, line 56 through col. 11, line 29 of reference [2]. This technique may provide increased image uniformity, but at the expense of frame rate, the possibility of misregistration between separate transmit events, and unnecessary agent destruction.

A need presently exists for an improved ultrasonic imaging method and apparatus (1) that provide improved axial resolution when detecting contrast agent, (2) that generate contrast-only images, background or anatomical reference images, and images that combine both contrast agent information and background or anatomical reference information efficiently and reliably, without requiring rescanning of the tissue. Preferably, this would be done while minimizing the undesired destruction of contrast agent during orientation scans conducted prior to the contrast agent imaging. Also, such a method and apparatus preferably offer excellent specificity for a contrast agent while maintaining acceptable tissue suppression, and they preferably function reliably over a large depth of field without unnecessary contrast agent destruction, significant image artifacts, or excessively degraded frame rate.

BRIEF SUMMARY

The systems described below produce images of contrast agents with diagnostic sensitivity, high specificity, excellent detail resolution, improved uniformity of detection, high frame rates, and the ability to separately display three types of images: contrast-only images, images that contain anatomical information only, and images that integrate anatomical information with detected contrast agent information. These systems further include a single user-interface switch that allows a clinician to quickly switch between the three different types of images during a contrast examination or after images of an examination have been stored.

DETAILED DESCRIPTION OF THE PRESENTLY PREFERRED EMBODIMENTS

Preferred Imaging System

Figure 1:
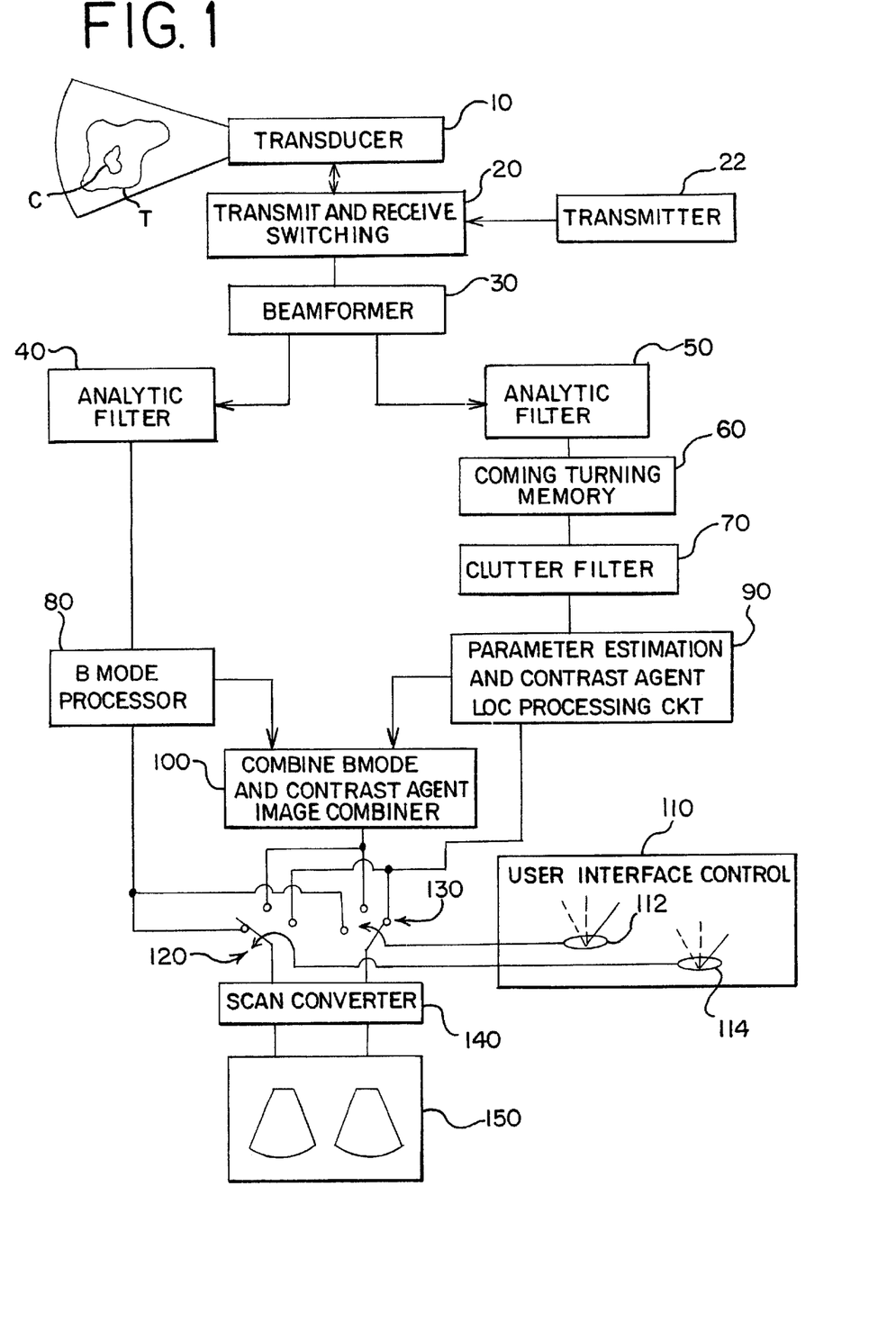
FIG. 1 is a block diagram of a medical ultrasonic imaging system that incorporates a preferred embodiment of this invention.

Turning now to the drawings, FIG. 1 shows a block diagram of a medical ultrasonic imaging system that incorporates a preferred embodiment of this invention. This imaging system includes a phased array ultrasonic transducer 10 that is coupled with transmit and receive switching circuitry 20. During transmit, the switching circuitry 20 connects a transmitter 22 to individual elements of the transducer array 10. The transmitter 22 applies excitation signals to the respective transducer elements to cause the transducer 10 to transmit and beam of ultrasonic energy into a tissue T comprising a contrast agent C. The contrast agent C can be any contrast agent that is suitable for use in the particular application. The contrast agent sold under the trade name Levovist can be taken as one example.

The tissue T and the contrast agent C generate echoes in response to each transmit pulse, and the transducer 10 generates echo signals that are connected by the switching circuitry 20 to a receiver 30 that includes a receive beamformer. The receive beamformer applies appropriate delays and phase changes to cause the echo signals to be summed coherently for selected points in space, in this example arranged along a scan line associated with each respective transmit event.

The transmitter 22 is programmed to transmit sets of two or more substantially identical transmit pulses (characterized by a fundamental frequency), and the receiver 30 generates sets of received pulses in response thereto. These received pulses are applied in parallel to first and second signal paths.

The first signal path includes an analytic filter 50, a corner turning memory 60, a clutter filter 70, and an LOC processing circuit 90. The analytic filter 50 passes a substantial portion of the energy of the received pulses at both the fundamental frequency and at one or more harmonic frequencies separated from the fundamental frequency. The analytic filter 50 can for example be an all-pass filter or a bandpass filter with a suitably large passband. As used herein, the term harmonic is intended broadly to encompass integer harmonics, subharmonics and ultraharmonics. Several alternative filter responses that can be used for the analytic filter 50 are discussed below.

The corner turning memory 60 can be a conventional element that selects filtered received pulses of a given set of received pulses and a selected range for further processing. The filtered received pulses are applied to the clutter filter 70, which is described in detail below. Generally speaking, the clutter filter (sometimes referred to as a wall filter) subtracts at least one received pulse from at least one other received pulse of the same set. For example, when each set of received pulses includes only two pulses, a clutter filter with the filter response [1–1] can be used. Similarly, when each set of received pulses includes only three pulses, the clutter filter 70 can provide the filter response [1–2 1]. In general, the clutter filter 70 may be an N-tap clutter filter, where N is equal to 2 or more.

The parameter estimator and contrast agent LOC processing circuit 90 processes the clutter-filtered, received pulses to generate contrast-specific image signals that are applied to switches 120, 130. These contrast-specific image signals selectively include echo signals associated with contrast agent, while substantially suppressing echo signals associated with tissue echoes, including tissue harmonic echoes. In particular, the initial received pulse in any given set will include echoes from contrast agent that is destroyed by the first transmit pulse, and thus the clutter filtered received pulses of a given set are contrast specific.

The LOC processing circuit 90 includes a detector such as for example a detector of the type commonly used in Doppler processing. Thus, the analytic filter 50, the corner turning memory 60 and the clutter filter 70 all operate on predetection ultrasonic signals.

The second signal path includes an analytic filter 40 and a B-mode processor 80. The analytic filter 40 can take any suitable form, and may be an all-pass filter or a bandpass filter centered on either the fundamental or a harmonic frequency. The B-mode processor 80 processes the filtered received pulses in the conventional manner to form B-mode image signals that are applied to the switches 120, 130.

The system of FIG. 1 also includes a third signal path that includes a combiner 100. The combiner 100 receives as inputs the B-mode image signals from the B-mode processor 80 and the contrast-specific image signals from the LOC processing circuit 90. The combiner 100 combines these two input image signals in any suitable manner and supplies the combined output to the switches 120, 130. The output image signal from the combiner 100 thus represents a composite signal including both tissue image features and contrast agent image features from the received pulses.

The switches 120, 130 and a scan converter 140 are included in an image processor that generates images for a display 150. The switch 120 controls the image displayed on the left-hand side of the display 150, and the switch 130 controls the image displayed on the right-hand side of the display 150. As explained above, both of the switches 120, 130 receive each of the three image signals as inputs (the contrast-specific image signal, the tissue or reference image signal, and the combined image signal). The states of the switches 120, 130 are controlled by a user interface control 110 that includes two control switches 112, 114. The control switches 112, 114 can take any suitable form, and for example can each be implemented as a rotary switch, as a set of push buttons, or as suitable control regions on a touch control screen. A user can use the control switch 112 to switch any one of the three image signals described above to the left-hand portion of the display 150, and the user can use the control switch 114 to command the display of any one of the three image signals on the right-hand side of the display 150.

The imaging system shown in FIG. 1 includes many components that are well known to those skilled in the art, and in general the widest variety of techniques can be used to implement the disclosed functions. For example, the transmitter 22 and the receiver 30 can be implemented using any desired analog or digital techniques. Any suitable transducer 10 can be used, including 1, 1.5 and 2 dimensional transducers of any desired curvature. The analytic filters 40, 50 can be implemented as FIR filters, as analog filters, and otherwise. The Corning turning memory 60, the clutter filter 70 and the LOC processing circuit 90 can be implemented for example using conventional Doppler processor techniques, and the B-mode processor 80 can be implemented using standard B-mode processing techniques. The combiner 100 can include any suitable system for combining the two input signals, including software-based systems, adders, multipliers, memories and the like. The switches 120, 130 may be implemented as mechanical switches or as logical branches in a digital processing method. Any suitable approach can be used for the scan converter 140 and the display 150.

Operation

Figure 11:
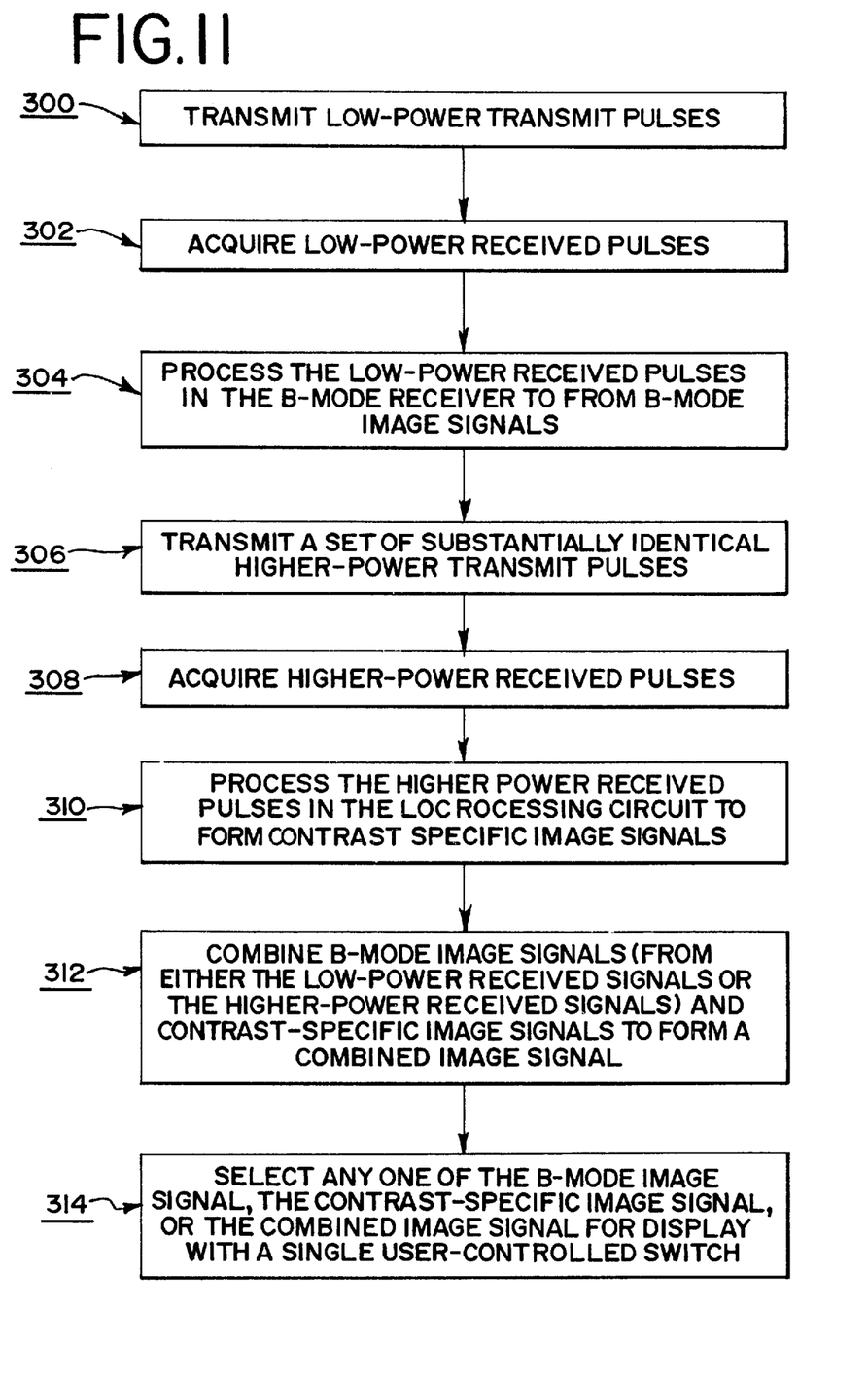
FIG. 11 is a flowchart illustrating one mode of operation of the system of FIG. 1.

FIG. 11 provides a flowchart illustrating one mode of operation of the system of FIG. 1. As shown in FIG. 11, a first step in this method is to transmit low-power transmit pulses in block 300 into the tissue containing the contrast agent. Low-power received pulses are acquired in block 302 and processed in block 304 in the B-mode processor 80 to form B-mode image signals. These B-mode image signals may be selected for display, and the low-power transmit pulses are selected to provide optimal B-mode images while destroying an acceptably low proportion of the contrast agent in the tissue. The B-mode image signals formed from the low-power received pulses are used to locate the transducer 10 and the scan plane appropriately prior to the initiation of contrast-specific imaging.

Once the transducer 10 and its scan plane have been appropriately positioned, the user then causes the transmitter 22 to transmit a set of substantially identical, higher-power transmit pulses in block 306. Corresponding higher-power received pulses are acquired in block 308 and processed in block 310 in the LOC processing circuit 90 to form contrast-specific image signals. Optionally, these higher-power received pulses may also be processed in the B-mode processor 80 to form B-mode image signals.

In block 312, B-mode image signals from the B-mode processor 80 and contrast-specific image signals from the LOC processing circuit 90 are combined to form a combined image signal. The B-mode image signals can be either B-mode image signals generated from the low-power received signals or B-mode image signals generated from the higher-power received signals. Since the higher-power received signals were acquired in response to transmit signals optimized for LOC processing, the B-mode signals from the lower-power transmit pulses may be preferred in many cases.

In block 314 any one of the B-mode image signal (based on either the low-power received pulses or the higher-power received pulses), the contrast-specific image signal, or the combined image signal may be selected for display with a single user-controlled switch.

Preferably, the switch also controls the transmitter 22 such that when the user selects a B-mode image signal only, the transmitter automatically operates to produce the low-power transmit pulses of block 300. Similarly, when the user selects either the contrast-specific image signal or the combined image signal, the transmitter is automatically controlled to generate the substantially identical, higher-powered transmit pulses of block 306. In this way, contrast agent is not depleted unnecessarily by high-power transmit pulses when the user is viewing only B-mode images. When a user requests the contrast-specific image signal or the combined image signal, the switch further allows the user to toggle between all three image signal types after all signals are received. The storage of all three types of image signals in a memory, such as a CINE memory, allows for easy review of any of the types of image signals after or in between real time scanning.

The system described above in conjunction with FIGS. 1 and 11 provides high-specificity contrast agent imaging using a coherent, multiple-pulse transmit and receive processing method. As explained above, substantially identical transmit pulses are used to acquire received pulses that are applied to a receive clutter filter that rejects slowly moving tissue as well as stationary tissue. Contrast agents are detected as a result of motion or a loss of correlation between received pulses, and contrast agents may for example be displayed as bright points against a darker image area that does not show substantial detected contrast agent. In this way, a contrast agent only image is generated by the LOC processing circuit 90 of FIG. 1. The system of FIG. 1, since it uses substantially identical transmit pulses, suppresses both fundamental and second harmonic signals returned from stationary or slowly moving structures with a simple clutter filter. The clutter filter 70 can take many forms, including those described in the following paragraphs.

Figure 2:
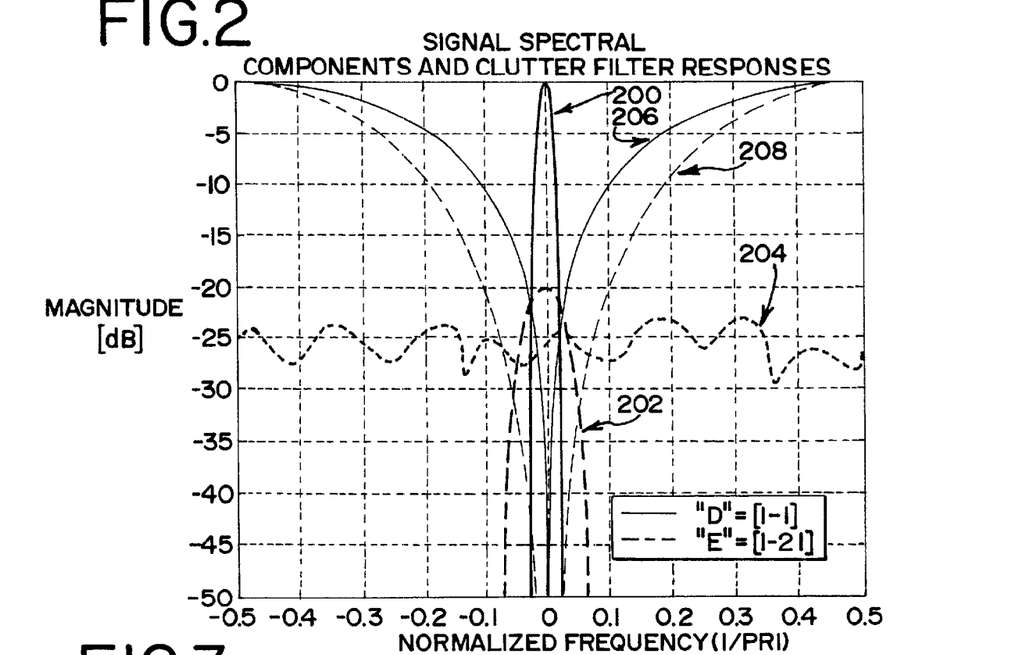
FIG. 2 is a graph illustrating the spectral distribution of various signals and filter responses.

FIG. 2 shows a spectral description of the signal components of a series of received pulses from a selected point from multiple transmit events down the same line. In FIG. 2, the abscissa shows the frequencies bounded by one half the inverse of the pulse repetition interval (PRI). The PRI is the inverse of the pulse repetition frequency (PRF), or the time between successive transmit event firings. The ordinate is the spectral signal strength for the graphed signal components and the degree of signal suppression for the graphed filter responses. Curve 200 of FIG. 2 is an example of a received fundamental signal from a stationary target such as the wall of a vessel in the liver. Curve 202 is an example of a received second harmonic signal due to energy from nonlinear propagation in tissue reflected from the same wall of the vessel. Curve 204 is an example of disrupted contrast agent near the vessel wall, but still within the acoustic beam pattern. Curve 206 is the filter response of clutter filter with an impulse response of [1-1].

With as few as two identical transmitted pulses per set, stationary or near-stationary structures can be suppressed by the simple clutter filter [1-1 ] and disrupted agent can be detected, since the decorrelation between the two received pulses generates spectral signal components within the passband of the filter. Without any motion between the two received pulses, stationary targets free of contrast agents appear as black in a detected image while disrupted agent shows up as bright areas. A preferred transmit and receive technique is the transmission of three identical pulses with a receive clutter filter impulse response of [1-2 1]. This filter response is shown in FIG. 2 as curve 208. The preferred filter response 208 provides superior motion or flash suppression. (Note that color or greyscale flash is caused by slowly moving targets from patient respiration and abrupt movements of the scanning transducer.) Although more than three identical pulses may be transmitted, filtered, and then displayed, three pulses are preferred since frame rates can be reduced with a larger number of transmitted pulses and unnecessary agent depletion can occur with more pulses.

Unlike prior-art techniques that alternate envelope polarities between transmitted pulses, the technique described above effectively suppresses stationary or near-stationary areas with insignificant contrast agent, since both reflected second harmonic signals generated from nonlinear propagation and reflected fundamental signals are suppressed.

Figure 3:
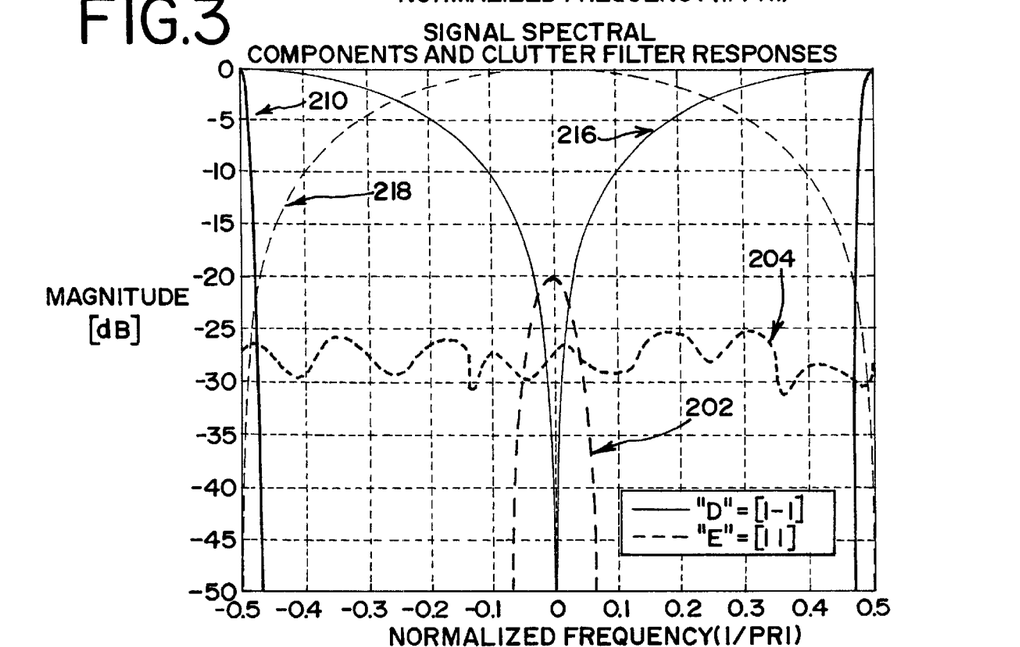
FIG. 3 is a graph illustrating the spectral distribution of selected signals generated using transmitted pulses of alternating polarities and related filter responses.

As shown in FIG. 3, prior-art techniques that alternate transmitted envelope polarities modulate the fundamental frequency signal components to half the inverse of the PRI. This requires a clutter filter that selectively suppresses energy at DC and half the inverse of the PRI. Notice for the use of two transmit events a two-coefficient clutter filter may suppress one, or the other, of the undesired spectral components, but not both. Filter impulse response 216 in FIG. 3 is identical to the curve 206 of FIG. 2, while filter impulse response 218 in FIG. 3 is a lowpass type filter response with coefficients [1 1]. A filter with filter response 218 inherently integrates the second harmonic signals from contrast agents and the signals from nonlinear acoustic propagation in tissue, and does not allow these two components to be accurately separated from one another. A filter with the filter response 216 integrates the second harmonic signals from contrast agent with fundamental signals. To maintain the same sensitivity to contrast agent disruption and similar suppression of tissue clutter and flash as the preferred technique disclosed above, at least one or more additional filter coefficients and at least one more transmit event are required, degrading frame rates and destroying agent undesirably.

The transmit and receive processing of FIG. 1 can be implemented using conventional color Doppler processing systems as described above; however, the use of only two or three transmitted pulses and receive clutter filters with only two or three coefficients is not generally used for non-contrast examinations since signal-to-noise (SNR) requirements demand between 6 and 16 pulses in each set. However, with the use of contrast agents during an examination the SNR is increased due to the strong reflections from gas-filled agents and fewer pulses may be used in each set. Thus, with the use of contrast agents during an examination the system of FIG. 1 can generate contrast-only images with high frames rates and high specificity that can be shown separately from anatomical images.

Since the system of FIG. 1 efficiently suppresses stationary or slowly moving targets and produces a contrast-only image, it provides a number of important benefits.

First, one or more separate, low-transmitted power images can be generated without significantly disrupting the available contrast agent. These low-power images may be conventional B-mode images showing anatomical information, as is standard in the medical industry, and they may be fundamental, harmonic, or other type of images. Such low-powered images may be generated with block 80 of FIG. 1. A fundamental-only image may be preferred since these types of images with the use of contrast agents will have inferior specificity for agent as compared to a second harmonic image. While operating at transmit power levels that do not significantly disrupt contrast agents, good image quality can still be maintained while a user pre-scans the area of interest.

Second, the system of FIG. 1 allows the preferred contrast agent imaging method to be activated by the user with a single key stroke. Since separate transmit events are used for generating the contrast-only image, these events can be initiated by a special button. This allows the user to locate an area of interest using low-powered images and then generate a contract-specific image, rather than searching for a suspicious area while contrast agent is being depleted by an "always on" contrast agent detection technique.

Figure 4:
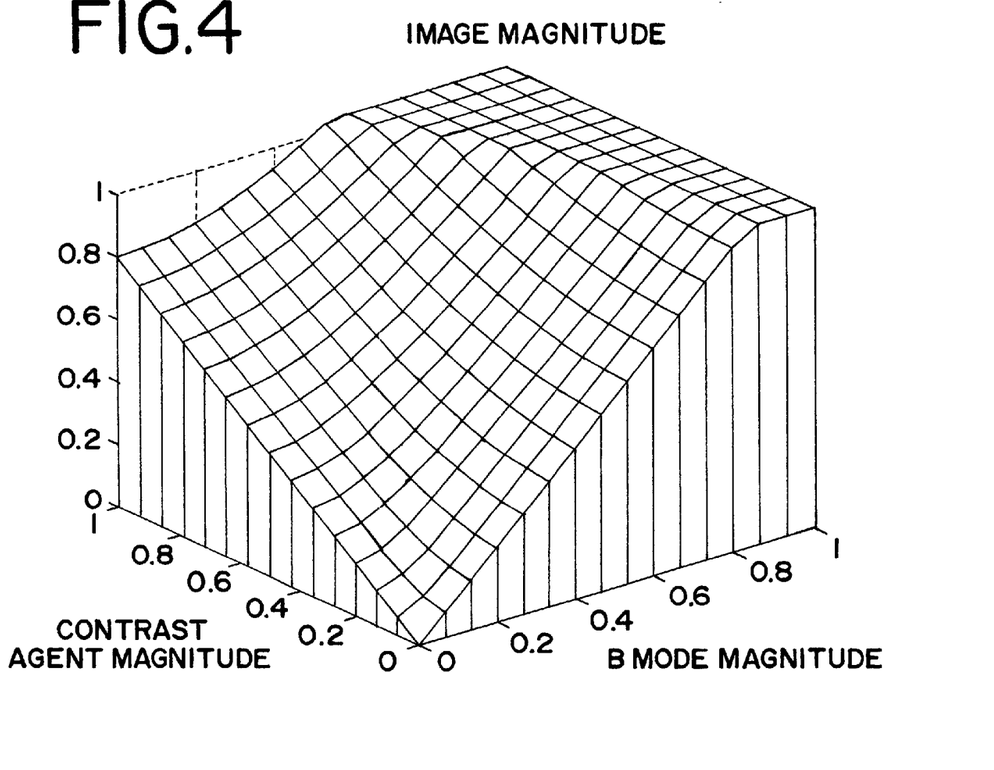
FIG. 4 is a graph illustrating a preferred function for combining contrast-specific image signals with anatomic image signals.

Third, the specificity for detected agent can be further increased by selectively combining the information from the separately generated reference anatomical image with the contrast-specific image in block 100 of FIG. 1. Different mathematical combinations or relationships between the background information and the contrast-specific information may be used. Examples include simple addition, subtraction, multiplication, division, and combinations of these functions which are dependent on the signal level in each type of image. Examples of suitable combinations are taught in the U.S. Pat. No. 5,961,460, which is hereby incorporated by reference. A preferred combination is shown in FIG. 4, in which magnitude of a point in the composite image generated by the combiner 100 is graphed in the vertical axis as a function of the magnitudes of the B-mode reference image signal and the contrast-specific image signal for the same point in the image.

Last, a user interface is further incorporated that allows a user the flexibility to select between three different types of images: (1) a contrast-specific image, (2) an anatomical image substantially free of detected agent, and (3) an image with anatomical information integrated with detected contrast agent information. These types of images can also be displayed in a dual screen format to facilitate visual registration of the same areas within two or more types of images. The user interface 110 of FIG. 1 provides buttons that allow each type of image to be displayed in each available screen format. Switches 120 and 130 select the appropriate image type. The physical implementation may be designed in many ways. For example, a simple memory unit can store the three available images, and keystrokes by the user on the user interface can direct a controller to read out the appropriate image from memory for display.

Along with the highly sensitive, highly specific, and flexible imaging method described above, the method further incorporates multiple harmonic signal components, thereby producing excellent detail resolution.

As described earlier, other prior-art harmonic imaging techniques selectively filter each received pulse and/or filter across multiple pulses at each range to suppress fundamental signal components. Prior-art single-pulse analytic filtering can efficiently reject fundamental signals and maintain harmonic signal components such as second harmonic signals, as shown in FIG. 5.

Figure 5:
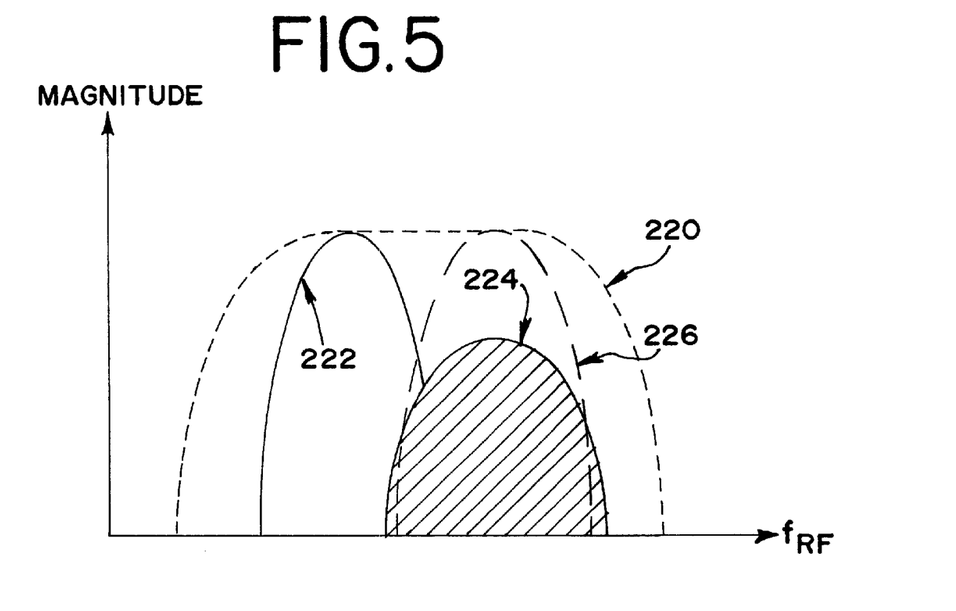
FIG. 5 is a graph showing filter responses suitable for single-pulse analytic filtering.

In FIG. 5 a representative frequency response of a phased array transducer is shown at 220. The abscissa defines the frequencies, $f_{RF}$, contained within a single received pulse. A broadband transmitted pulse provides energy for dominant fundamental 222 and second harmonic 224 received signal energy from contrast agents in the acoustic field. A simple filter response 226 is used to suppress the fundamental energy and improve the detection of contrast agent since the ratio of second harmonic returns from contrast agents relative to second harmonic returns from tissue will be larger than the ratio of fundamental returns from contrast agents relative to fundamental returns from tissue. This filtering may be centered about the received second harmonic frequencies, about an intermediate frequency where the fundamental and harmonic frequencies have been mixed down, or about DC after mixing the fundamental and harmonic frequencies to baseband. These are all well known methods of signal processing. The Pulse Inversion, Pulse Inversion Doppler, and Phase Inversion techniques that alternate the envelope polarity between transmitted pulses use the combination of pulses to suppress fundamental signal energy. This combination step is provided by a clutter filter as described earlier; see for example, the filter response 218 in FIG. 3. This is a second means to selectively suppress fundamental energy. Both means can be used together to selectively suppress fundamental signal energy.

The system of FIG. 1 does not selectively suppress substantial fundamental signal components, but preferentially maintains multiple harmonic signal components including the fundamental signal components. Since stationary tissue, slowly moving tissue, or more abrupt movements of tissue that could cause color flash are suppressed by the preferred clutter filtering described above, fundamental signal energy from contrast agents is not substantially suppressed by the single pulse filter 50 of FIG. 1, but rather it is maintained. Maximal signal bandwidths are maintained, producing high resolution images of contrast agents. The resolution is no longer determined by the second harmonic energy alone, but instead is determined by the broad combination of the fundamental energy and the energy of at least one harmonic of the fundamental energy.

Preferred Embodiments of the Filter 50

Figure 6:
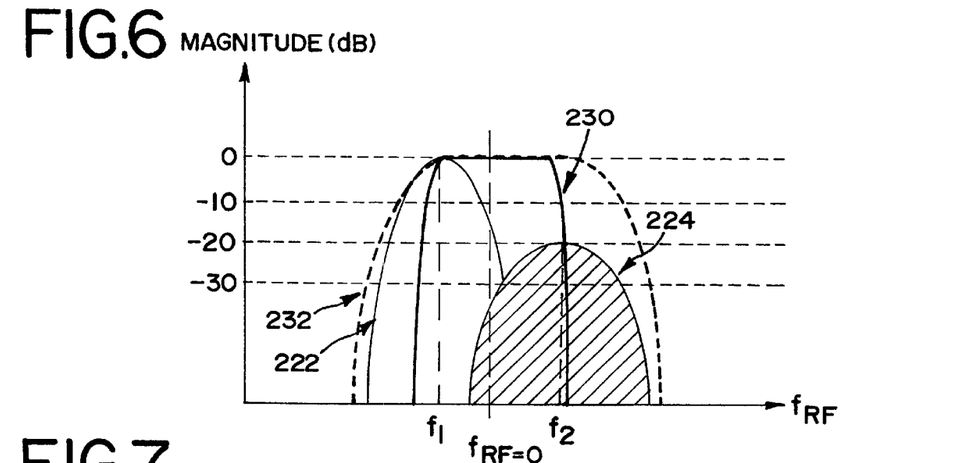
FIG. 6 is a graph illustrating two signal responses suitable for the analytic filter 50 of FIG. 1.

In one embodiment of the filter 50 of FIG. 1, substantial fundamental and second harmonic signal components are maintained, as illustrated in FIG. 6. In FIG. 6, substantial amounts of fundamental signal 222 and second harmonic signal 224 are allowed to pass through the filter response 230 or filter response 232. Filter response 230 may be preferred for improved SNR relative to filter response 232, and the exact filter is best determined based upon the type of contrast agent, the clinical application, and frequency response of the transducer and system. A "substantial" amount of signal energy is defined as half or more of the signal energy within a frequency band of interest. A frequency band of interest may be a fundamental frequency band centered about a particular frequency. A frequency band of interest may also be a harmonic frequency band such as a second harmonic, subharmonic, ultraharmonic, etc. The frequency bands may be symmetric or asymmetric. In FIG. 6, the filter response 230 allows a substantial amount of the fundamental energy to pass through the filter, since the lower frequency transition region at the −10 dB level is located at a frequency lower than the center frequency f1 of the fundamental frequency band. In this example, it was assumed that the fundamental frequency band was symmetric such that the filter passes at least half of the fundamental energy. Asymmetric responses are also included within the scope of this invention. Substantial amounts of second harmonic energy are also passed based on this definition since the −10 dB level relative to the peak second harmonic spectral level of the higher frequency transition region falls above the center frequency f2 of the harmonic frequency band. Filter response 232 is a preferred response for the filter 50 since it maintains signal energy and resolution. High resolution images are generated since the signal energy made available by the filter exists over a large bandwidth including substantial fundamental and substantial second harmonic frequencies.

Figure 7:
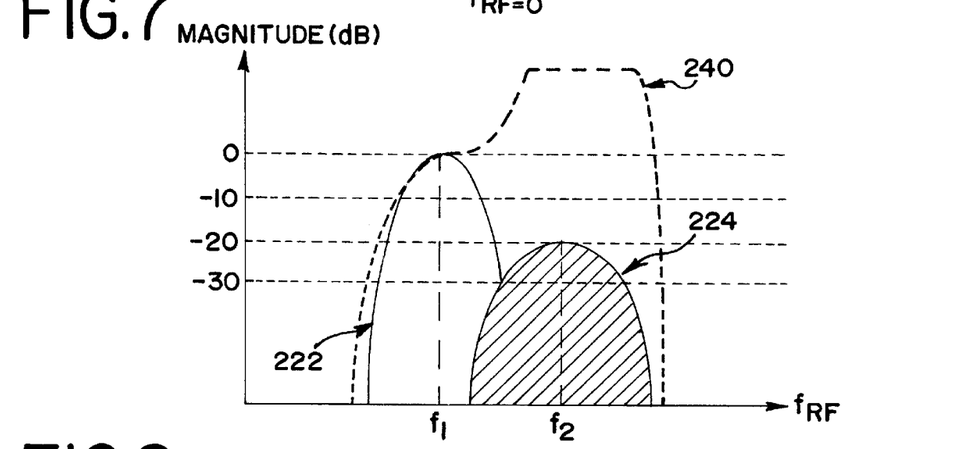
FIG. 7 is a graph illustrating another filter response suitable for use in the analytic filter 50 of FIG. 1.

Filter responses that produce similar post-filtered signal energy between two or more different frequency bands of interest may be used to maximize resolution. This equalization process can be used to maximize the resolution at a desired signal level such as the −6 dB level relative to the peak signal in the fundamental frequency band. FIG. 7 shows an example of a filter response 240 that boosts second harmonic energy. The corresponding filter can be used for the filter 50.

The filter response 240 preferentially increases the signal strength around second harmonic frequencies centered about the frequency f2. In this example, the signal returns from a particular contrast agent produce second harmonic signals 20 dB smaller than fundamental returns, and the filter response 240 boosts the second harmonic signals by 20 dB. The optimum filter response will be dependent upon the type of contrast agent and the clinical application.

The filter response may also be adaptively selected based on signal returns while using a symmetric filter response. For example, the analytic filter 50 of FIG. 1 may include two or more filters, including first and second filters. In this example, the first filter is a narrowband filter designed to suppress fundamental signals and to pass second harmonic signals, thereby allowing detection of substantial second harmonic signals. The second filter is a second narrowband filter designed to preferentially detect fundamental signals by suppressing second harmonic signals. The ratio of the two post-filtered signals from each of these two narrowband filters is used to select a single broadband "equalization" filter. As illustrated in FIG. 7, the ratio of signals from the two narrowband filters in this example is preferably 20 dB for the filter response 240.

Figure 8:
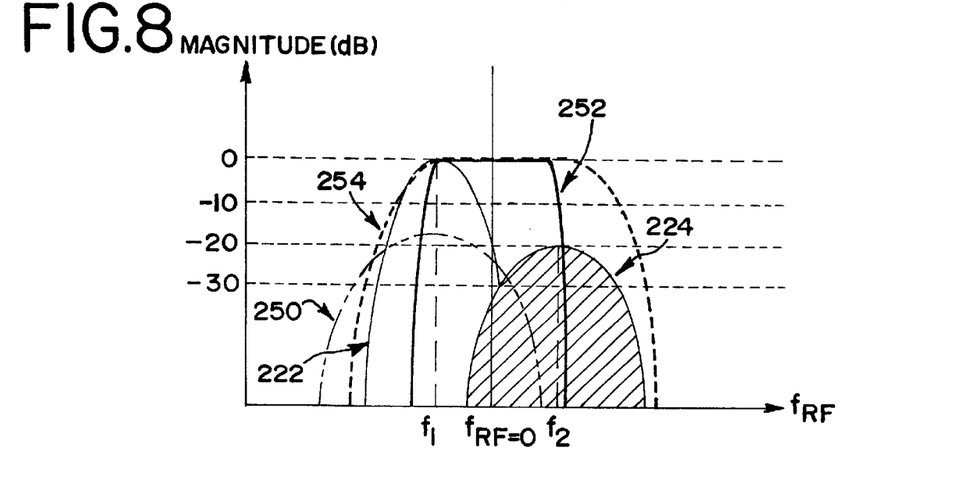
FIG. 8 is a graph illustrating further filter responses suitable for use in the analytic filter 50 of FIG. 1.

In another embodiment, substantial amounts of other harmonic frequency bands can be passed by the filter 50. For example, as shown in FIG. 8, cubic fundamental energy 250, fundamental energy 222, and second harmonic energy 224 can be selectively passed by a filter response 252 or 254 to produce excellent signal energy and resolution. (Cubic fundamental energy is energy generated by a nonlinear process of third order that exists within the fundamental frequency band rather than a third harmonic frequency band. U.S. Pat. application Ser. No. 09/514,803 describes this type of nonlinear signal energy in greater detail and is incorporated herein by reference.) In this example the original analytic received signal has been demodulated to baseband such that the cubic fundamental and fundamental signals are centered about the frequencies below DC ($f_{RF}=0$) while the second harmonic signals are centered about the frequencies above DC.

The broadband receive filtering of the filter 50 may be applied to each received signal on each system channel and/or after complete or partial receive beamformation.

Preferred Transmit Pulses

The system of FIG. 1 is preferably designed to produce more uniform detection of contrast agents with high sensitivity and high specificity while maintaining excellent resolution due to the use of substantial amounts of fundamental signal energy as well as at least one harmonic frequency band of the fundamental signal energy. A transmit field that contains at least two spatially distinct focal zones along a scan line and that is generated from a single transmit event can be combined with the above method for detecting contrast agents.

The harmonic imaging techniques discussed above that do not alternate the envelope polarity between transmitted pulses lack the excellent detail resolution of the inventive method, since they rely upon narrowband signals and the selective suppression of fundamental signals. Techniques that alternate the envelope polarity between transmitted pulses improve detail resolution with more broadband pulses and clutter filtering that selectively suppresses fundamental signal energy; however, some SNR is lost due to the shorter pulses and less transmitted energy. Thus, these two approaches to the imaging of contrast agent suffer from either suboptimal resolution or detectability over only a small area of interest, or depth-of-field. With the contrast agent imaging method of FIG. 1, detectability may also be optimal over only a small area around the transmit focal region since broadband short pulses are preferred; however, the incorporation of multiple simultaneously transmitted beams can more uniformly distribute peak pressure over an area of interest, generating detectability over a larger area, or depth-of-field, in an image with the benefits already disclosed.

Figure 9:
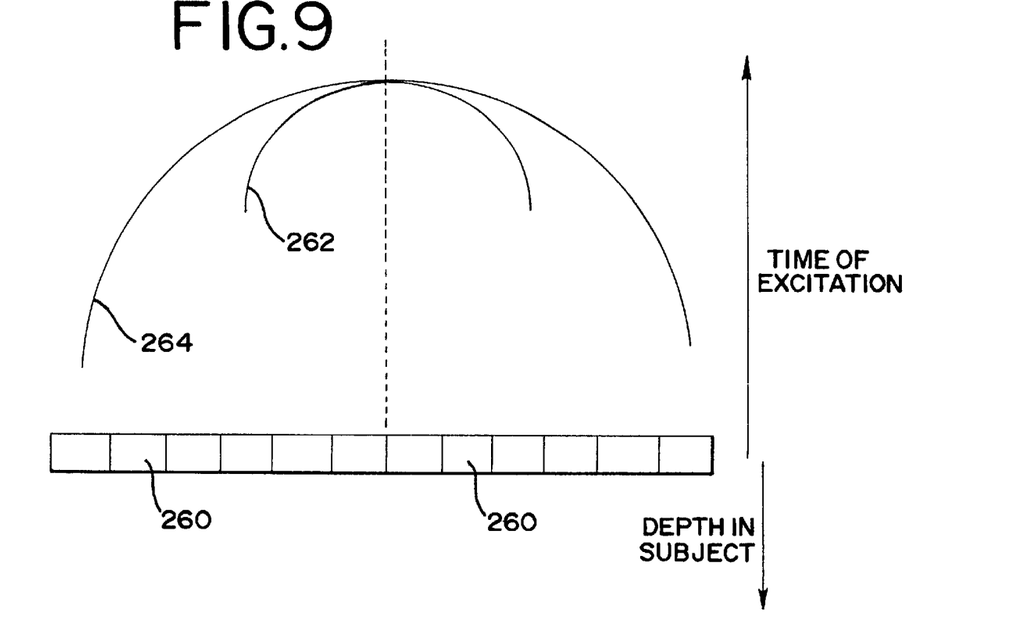
FIG. 9 is a schematic diagram illustrating delay profiles suitable for use in the transmitter of FIG. 1.

Transmitted field patterns that focus transmitted ultrasonic energy over at least two spatially distinct focal regions can be generated during a single transmit event by appropriately defining the firing sequence of each element in a phased array transducer. More than one delay profile across the set of active transducer elements may be used to focus acoustic energy over at least two spatially distinct focal zones. In this case, some elements will be excited by two or more waveforms separated in time. Other elements will be excited by two or more waveforms that are not separated in time. Still other elements will be excited by only one waveform corresponding to a single focal zone. An example of a pair of delay profiles is shown in FIG. 9, in which the elements 260 of the transducer 10 are shown. The line 262 corresponds to the center of a delay profile of a set of excitation waveforms. The excitation waveforms are not shown but may be of any type or shape. Line 264 is a second delay profile for a deeper focal zone using a larger number of transducer elements.

Figure 10:
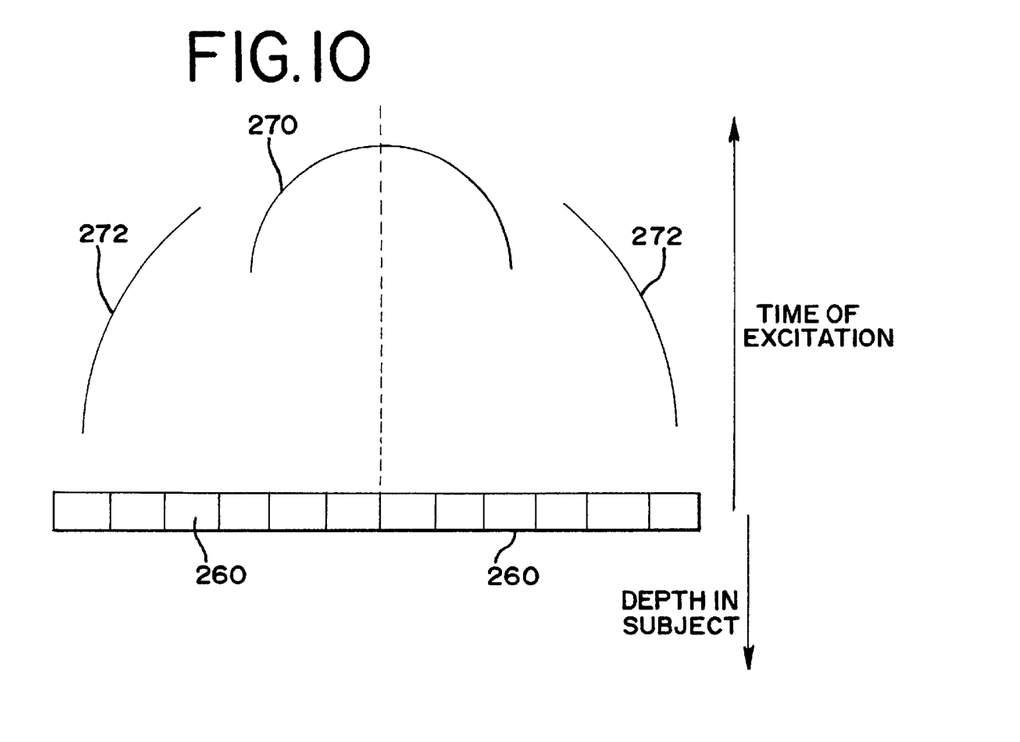
FIG. 10 is a schematic view illustrating another time delay profile suitable for use in the transmitter of FIG. 1.

A single delay profile can also be used to selectively focus ultrasonic energy at more than one focal zone. The single delay profile can contain discontinuities that segment the profile into sections that focus at different locations. Some elements focus at one focal zone while other elements focus at a different focal zone. An example incorporating two spatially distinct focal zones is shown by curves 270 and 272 in FIG. 10. This latter approach is more easily implemented on systems that can only program one identical waveform into each active element in a transducer. The approach shown in FIG. 9 can require a different waveform for each element, thereby increasing the complexity and cost of the system.

Examples of transmit beamformers and methods to generate more uniform peak pressure over a greater depth of field are further described in U.S. Pat. applications Ser. Nos. 09/253,088 and 09/404,089, which are hereby incorporated by reference in their entirety.

Additionally, coded transmit pulses can be used to improve SNR and image uniformity while maintaining high resolution. When the transmit pulses used in the system of FIG. 1 are not limited by spatial peak temporal average intensity (Ispta) maxima, electrical power, or thermal maxima, additional energy may be transmitted with coded excitation. Coded excitation techniques are described in more detail in pending U.S. application Ser. No. 09/283,346, which is hereby incorporated by reference.

Concluding Remarks

It should be apparent from the foregoing that an improved method and apparatus have been described that allow contrast agent to be imaged with high specificity, that improve the flexibility with which contrast specific and B-mode reference images can be displayed, that produce a combined B-mode and contrast specific image for display, and that provide a high contrast sensitivity over a large portion of the imaged region.

are set to be coupled together may be coupled together directly or indirectly (via one or more intervening but unnamed elements).

Various ones of the features described above can be used independently of one another. For example, the contrast-specific image signal generated by the circuit 90 may be processed for display in any desired way, with or without other image signals such as the image signals generated by the elements 80, 100. Also, the improved image selection techniques described above in connection with the elements 110, 120, 130 may be used with other systems for generating contrast-specific images.

The foregoing detailed description has discussed only a few of the many forms that the present invention can take. This detailed description is therefore intended by way of illustration and not by way of limitation. It is only the following claims, including all equivalents, that are intended to define the scope of this invention.

TABLE 1

[1] "Harmonic Power Mode Doppler Using Microbubble Contrast Agents: An Improved Method for Small Vessel Flow Imaging" by Peter Burns, J. Powers, D. Simpson, A. Brezina, A. Kolin, C. Chin, V. Uhlendorf, and T. Fritzsch; 1994 Ultrasonics Symposium, Nov. 1–4, 1994, Hotel Martinez, Cannes, France; An International Conference of the IEEE Ultrasonics, Ferroelectrics, and Frequency Control Society.
[2] "Ultrasonic Diagnostic Imaging with Contrast Agents", U.S. Pat. No. 5,833,613, Filed Sep. 27, 1996; Issued Nov. 10, 1998; Inventors: Michalakis Averkiou, Matthew Bruce, Jeffry Powers; Assignee: Advanced Technology Laboratories.
[3] "Ultrasonic Diagnostic Imaging with Harmonic Contrast Agents", U.S. Pat. No. 5,706,819; Filed Oct. 9, 1996; Issued Jan. 13, 1998; Inventors: Juin-Jet Hwang and David Hope Simpson; Assignee: Advanced Technology Laboratories.
[4] "Two Pulse Technique for Ultrasonic Harmonic Imaging", U.S. Pat. No. 5,951,478; Filed Dec. 8, 1997; Issued Sept. 14, 1999; Inventors: Juin-Jet Hwang and David Hope Simpson; Assignee: Advanced Technology Laboratories.
[5] "Ultrasound Imaging System Employing Phase Inversion Subtraction to Enhance the Image", U.S. Pat. No. 5,632,277; Filed June 28, 1996; Issued May 27, 1997; Inventors: Christopher S. Chapman and John C. Lazenby; Assignee: Siemens Medical Systems.
[6] "Pulse Inversion Doppler Ultrasonic Diagnostic Imaging", U.S. Pat. No. 6,095,980, Filed Sept. 17, 1998; Issued Aug. 1, 2000; Inventors: Peter N. Burns and David Hope-Simpson; Assignee: Sunnybrook Health Science Centre.
[7] "Medical Diagnostic Ultrasound System Using Contrast Pulse Sequence Imaging", U.S. patent application Ser. No. 09/514,803, filed February 29, 2000; Inventor: Thomas; Assignee: Acuson.
[8] "Methods of and Systems for Examining Tissue Perfusion Using Ultrasonic Contrast Agents", U.S. Pat. No. 5,255,683; filed Dec. 30, 1991; Issued Oct. 26, 1993; Inventor: Monaghan; Assignee: Sound Science Limited Partnership.
[9] "Ultrasonic Detection of Contrast Agents", U.S. Pat. No. 5,456,257, filed Nov. 23, 1994; Issued Oct. 10, 1995; Inventors: Keith Johnson and Jeffry Powers; Assignee: Advanced Technology Laboratories.
[10] "Ultrasound Imaging Enhancement Methods and Systems", U.S. Pat. No. 5,961,460; Filed April 11, 1997; Issued October 5, 1999; Inventors: Ismayil Guracar, Gregory Holley, Ting-Lan Ji, and Bhaskar Ramamurthy; Assignee: Acuson.

As used herein the term "tissue" is intended to encompass the widest range of biological tissues, including blood and contrast agent contained within the tissue.

The term "set" is intended broadly to encompass two or more.

The term "filter" is intended broadly to encompass filter assemblies that include two or more filters.

The term "harmonic" is intended broadly to encompass integer harmonics, subharmonics and ultraharmonics.

The term "switch" is intended broadly to encompass the widest variety of devices for selecting among several inputs, including analog switches, digital switches and software systems that perform a switching function.

The term "coupled" is intended broadly to encompass both direct and indirect coupling. Thus, two elements that

What is claimed is:
1. A medical ultrasonic imaging method comprising:
    (a) transmitting a set of at least two substantially identical ultrasonic transmit pulses into a tissue comprising a contrast agent, said transmit pulses characterized by a fundamental frequency;
    (b) acquiring a set of received pulses from the tissue, each of the received pulses associated with a respective one of the transmit pulses;
    (c) filtering the received pulses with a filter that passes a substantial portion of energy of the received pulses at the fundamental frequency as well as a substantial portion of energy of the received pulses at a harmonic of the fundamental frequency separated in frequency from the fundamental frequency;

(d) applying the filtered received pulses of (c) to a clutter filter; and (e) detecting the clutter-filtered received pulses of (d).

2. The method of claim 1 wherein the filter of (c) passes all ultrasonic frequencies of the received pulses.

3. The method of claim 1 wherein the filter of (c) comprises an equalization filter.

4. The method of claim 1 wherein the filter of (c) comprises a bandpass filter.

5. The method of claim 1 wherein the filter of (c) passes a substantial portion of energy of the received pulses at a harmonic of the fundamental frequency selected from the group consisting of: an integer harmonic of the fundamental frequency, a subharmonic of the fundamental frequency, an ultraharmonic of the fundamental frequency, and combinations thereof.

6. The method of claim 1 wherein the clutter filter of (d) comprises a clutter filter.

7. The method of claim 1 wherein the clutter filter of (d) comprises a clutter filter.

8. The method of claim 1 wherein the clutter filter of (d) comprises an N-tap clutter filter.

9. The method of claim 1 wherein the transmit pulses of (a) comprise coded transmit pulses.

10. The method of claim 1 wherein (a) comprises applying a plurality of excitation waveforms to a plurality of transducer elements of a phased-array transducer.

11. The method of claim 1 wherein the transmit pulses of (a) are each characterized by at least two spatially distinct focal zones.

12. The method of claim 1 wherein the transmit pulses of (a) are each characterized by at least three spatially distinct focal zones.

13. The method of claim 1 wherein the transmit pulses of (a) are each characterized by more than three spatially distinct focal zones.

14. The method of claim 1 further comprising:

(f) processing at least some of the received pulses of the set in a second signal path for display and combination with the clutter-filtered received pulses.

15. The method of claim 1 further comprising:

(f) transmitting additional ultrasonic transmit pulses into the tissue;

(g) acquiring additional received pulses from the tissue in response to the additional transmit pulses; and (h) processing the additional received pulses in a second signal path for display and combination with the clutter-filtered received pulses.

16. The method of claim 15 wherein acts (f) and (g) are performed before acts (a) and (b); and wherein the additional ultrasonic transmit pulses of (f) are lower in power than the transmit pulses of (a).

17. The method of claim 1 further comprising:

(f) processing the received pulses in a second signal path; and (g) combining the detected, clutter-filtered received pulses of (e) with the processed received pulses of (f); and (h) processing the combined received pulses of (g) for display.

18. The method of claim 1 further comprising:

(f) transmitting additional ultrasonic transmit pulses into the tissue;

(g) acquiring additional received pulses from the tissue in response to the additional transmit pulses;

(h) processing the additional received pulses in a second signal path;

(i) combining the detected, clutter-filtered received pulses of (e) with the processed received pulses of (h); and (j) processing the combined received pulses of (i) for display.

19. The method of claim 18 wherein acts (f) and (g) are performed before acts (a) and (b); and wherein the additional ultrasonic transmit pulses of (f) are lower in power than the transmit pulses of (a).

20. A medical ultrasonic imaging system comprising:

a phased-array transducer;

a transmitter coupled with the transducer and operative to transmit a set of two or more substantially identical ultrasonic transmit pulses into a tissue comprising a contrast agent, said transmit pulses characterized by a fundamental frequency;

a receiver coupled with the transducer and operative to acquire a set of received pulses from the tissue, each of the received pulses associated with a respective one of the transmit pulses;

a first filter coupled with the receiver to filter the received pulses, said filter operative to pass a substantial portion of energy of the received pulses at the fundamental frequency as well as a substantial portion of energy of the received pulses at a harmonic of the fundamental frequency separated in frequency from the fundamental frequency;

a clutter filter coupled with the first filter and operative to combine the filtered received pulses to detect a loss of correlation among the filtered receive signals of the set; and a detector coupled with the clutter filter and operative to detect the clutter-filtered receive signals.

21. The invention of claim 20 wherein the first filter passes all ultrasonic frequencies of the received pulses.

22. The invention of claim 20 wherein the first filter comprises an equalization filter.

23. The invention of claim 20 wherein the first filter comprises a bandpass filter.

24. The invention of claim 20 wherein the first filter passes a substantial portion of energy of the received pulses at a harmonic of the fundamental frequency selected from the group consisting of: an integer harmonic of the fundamental frequency, a subharmonic of the fundamental frequency, an ultraharmonic of fundamental frequency, and combinations thereof.

25. The invention of claim 20 wherein the clutter filter comprises a clutter filter.

26. The invention of claim 20 wherein the clutter filter comprises a clutter filter.

27. The invention of claim 20 wherein the clutter filter comprises an N-tap clutter filter.

28. The invention of claim 20 wherein the transmitter is operative to transmit coded transmit pulses.

29. The invention of claim 20 wherein the transmitter is operative to apply respective excitation waveforms to individual transducer elements included in the phased array transducer.

30. The invention of claim 20 wherein the transmitter is operative to provide the transmit pulses with at least two spatially distinct focal zones.

31. The invention of claim 20 wherein the transmitter is operative to provide the transmit pulses with at least three spatially distinct focal zones.

32. The invention of claim 20 wherein the transmitter is operative to provide each of the transmit pulses with more than three spatially distinct focal zones.

33. The invention of claim 20 further comprising a second processing path coupled to the receiver and operative to process at least some of the received pulses for display and combination with the clutter-filtered received pulses.

34. The invention of claim 20 further comprising a second processing path coupled to the receiver and operative to process additional received pulses for display and combination with the clutter-filtered received pulses.

35. The invention of claim 20 further comprising:
a second signal path coupled to the receiver and operative to process the received pulses for display; and
a combiner operative to combine the detected, clutter-filtered received pulses with the received pulses processed in the second signal path.

36. The invention of claim 20 further comprising:
a second signal path coupled to the receiver and operative to process additional received pulses for display; and
a combiner operative to combine the detected, clutter-filtered received pulses with the additional received pulses processed in the second signal path.

37. A medical ultrasonic imaging method comprising:
(a) transmitting a plurality of ultrasonic transmit pulses into a tissue comprising a contrast agent;
(b) acquiring a plurality of received pulses from the tissue, each of the received pulses associated with a respective one of the transmit pulses;
(c) forming a first image signal from at least some of the received pulses, said first image signal selectively emphasizing contrast agent echoes;
(d) forming a second image signal from at least some of the received pulses, said second image signal selectively emphasizing tissue echoes;
(e) forming a third image signal from at least some of the received pulses, said third image signal emphasizing both contrast agent echoes and tissue echoes; and
(f) selecting any one of the first, second and third image signals for display using a single user-controlled switch.

38. The method of claim 37 wherein the plurality of transmit pulses comprise a set of at least two substantially identical transmit pulses.

39. The method of claim 38 wherein the plurality of transmit pulses additionally comprise a low-power transmit pulse characterized by a lower transmit power than the substantially identical transmit pulses.

40. A medical ultrasonic imaging system comprising:
a phased-array transducer;
a transmitter coupled with the transducer and operative to transmit a plurality of ultrasonic transmit pulses into a tissue comprising a contrast agent;
a receiver coupled with the transducer and operative to acquire a set of received pulses from the tissue, each of the received pulses associated with a respective one of the transmit pulses;
a first signal path coupled with the receiver and operative to form a first image signal from at least some of the received pulses, said first image signal selectively emphasizing contrast agent echoes;
a second signal path coupled with the receiver and operative to form a second image signal from at least some of the received pulses, said second image signal selectively emphasizing tissue echoes;
a third signal path coupled with the receiver and operative to form a third image signal from at least some of the received pulses, said third image signal emphasizing both contrast agent echoes and tissue echoes;
an image processor responsive to the first, second and third image signals; and
a user-controlled switch coupled with the image processor and operative to select any one of the first, second, and third image signals for display.

41. The invention of claim 40 wherein the plurality of transmit pulses comprise a set of at least two substantially identical transmit pulses.

42. The invention of claim 41 wherein the plurality of transmit pulses additionally comprise a low-power transmit pulse characterized by a lower transmit power than the substantially identical transmit pulses.

* * * * *